United States Patent
Ishii et al.

(10) Patent No.: US 8,212,085 B2
(45) Date of Patent: Jul. 3, 2012

(54) METHOD FOR PURIFYING OPTICALLY ACTIVE 1-(2-TRIFLUOROMETHYLPHENYL)ETHANOL

(75) Inventors: Akihiro Ishii, Saitama (JP); Hideyuki Tsuruta, Fujimino (JP)

(73) Assignee: Central Glass Company, Limited, Ube-shi (JP)

( * ) Notice: Subject to any disclaimer, the term of this patent is extended or adjusted under 35 U.S.C. 154(b) by 169 days.

(21) Appl. No.: 12/863,121

(22) PCT Filed: Jan. 20, 2009

(86) PCT No.: PCT/JP2009/050746
§ 371 (c)(1),
(2), (4) Date: Jul. 15, 2010

(87) PCT Pub. No.: WO2009/098935
PCT Pub. Date: Aug. 13, 2009

(65) Prior Publication Data
US 2011/0054223 A1    Mar. 3, 2011

(30) Foreign Application Priority Data

Feb. 5, 2008 (JP) ................................ 2008-024867

(51) Int. Cl.
*C07C 29/78* (2006.01)
(52) U.S. Cl. ...................................................... 568/810
(58) Field of Classification Search .................. 568/810
See application file for complete search history.

(56) References Cited

U.S. PATENT DOCUMENTS

| | | | |
|---|---|---|---|
| 5,395,983 A | 3/1995 | Miyazawa et al. | |
| 2002/0016511 A1 | 2/2002 | Ishii et al. | |
| 2002/0103400 A1 | 8/2002 | Ishii et al. | |
| 2009/0240087 A1 | 9/2009 | Ishii et al. | |

FOREIGN PATENT DOCUMENTS

| | | |
|---|---|---|
| JP | 5-208927 A | 8/1993 |
| JP | 2002-30020 A | 1/2002 |
| JP | 2002-187873 A | 7/2002 |
| JP | 2003-226659 A | 8/2003 |
| JP | 2007-106702 A | 4/2007 |
| WO | WO 2007/030359 A1 | 3/2007 |

OTHER PUBLICATIONS

Karl B. Hansen, et al. "Scalable, efficient process for the synthesis of (R)-3.5-bistrifluoromethylphenyl ethanol via catalytic asymmetric transfer hydrogenation and isolation as a DABCO inclusion complex", Tetrahedron: Asymmetry, 2003, pp. 3581-3587, vol. 14, U.K.
C. Cardellicchio, et al., "Functionalized Ketones by Iron Mediated Reaction of Grignard Reagents with ACYL Chlorides" Tetrahedron Letters, 1987, pp. 2053-2056, vol. 28, No. 18, U.K.
Iwao Ojima, Catalytic Asymmetric Synthesis, Second Edition, 2000, Wiley-VCH, Inc, p. 34-82.
International Search Report including partial English translation dated Apr. 21, 2009 and PCT/ISA/237 Form (Twelve (12) pages).

*Primary Examiner* — Sikarl Witherspoon
(74) *Attorney, Agent, or Firm* — Crowell & Moring LLP

(57) ABSTRACT

There is disclosed a purification method of an optically active 1-(2-trifluoromethylphenyl)ethanol represented by the formula [1], which includes recrystallizing the optically active 1-(2-trifluoromethylphenyl)ethanol from an aliphatic hydrocarbon solvent

[Chem. 11]

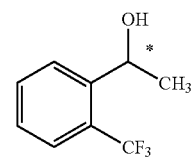

[1]

where * denotes an asymmetric carbon.
This method makes it possible to improve the optical purity of the ethanol significantly.

7 Claims, No Drawings

METHOD FOR PURIFYING OPTICALLY ACTIVE 1-(2-TRIFLUOROMETHYLPHENYL)ETHANOL

TECHNICAL FIELD

The present invention relates to an industrial purification method of an optically active 1-(2-trifluoromethylphenyl) ethanol, which is important as an intermediate for medicines.

BACKGROUND ART

An optically active 1-(2-trifluoromethylphenyl)ethanol is important as an intermediate for medicines (cf. Patent Document 1). Optically active 1-phenyl ethanols can be produced by chemical or biological asymmetric reduction of corresponding acetophenones. It is however difficult only by such asymmetric reduction reaction that the resulting reaction product satisfies the level of optical purity required for use as an intermediate for medicines. In order to obtain the product of desired optical purity, there is a need to perform purification such as conversion of the reaction product to a derivative thereof and kinetic resolution of the reaction product in combination with the asymmetric reduction reaction. The above purification operation results in not only a deterioration of productivity due to an increase in the number of operation steps but also a decrease of total yield and an increase of waste. It is thus important in this field to find out how to improve the optical purity of the asymmetric reduction product efficiently by simple operation.

There is no report of any purification method by which the optical purity of the target compound of the present invention, an optically active 1-(2-trifluoromethylphenyl)ethanol, can be improved efficiently by simple operation.

A purification method of a similar compound, an optically active 1-(3,5-bistrifluoromethylphenyl)ethanol, is already reported (cf. Non Patent Document 1). As the optically active 1-(3,5-bistrifluoromethylphenyl)ethanol gets preferentially deposited in racemic crystal form by recrystallization, it is impossible to efficiently improve the optical purity of the 1-(3,5-bistrifluoromethylphenyl)ethanol by recrystallization. The optical purity of the optically active 1-(3,5-bistrifluoromethylphenyl)ethanol is thus improved by recrystallizing a complex of the optically active 1-(3,5-bistrifluoromethylphenyl)ethanol and DABCO (1,4-diazabicyclo[2.2.2]octane) (1-(3,5-bistrifluoromethylphenyl)ethanol: DABCO=2:1). In this method, however, it is necessary to use 0.5 equivalent weight of the relatively expensive DABCO and to recover the optically active 1-(3,5-bistrifluoromethylphenyl)ethanol from the complex after the recrystallization.

Further, the present applicant has disclosed that it is not possible to improve the optical purity of either of an optically active 1-(3-trifluoromethylphenyl)ethanol and an optically active 1-(4-trifluoromethylphenyl)ethanol efficiently only by recrystallization. The optically active 1-(3-trifluoromethylphenyl)ethanol does not get favorably deposited in crystal form by recrystallization (cf. Reference examples 3 to 6 in TABLE 3). The optically active 1-(4-trifluoromethylphenyl) ethanol cannot be obtained with high optical purity by recrystallization (cf. Reference examples 7 to 10 in TABLE 4).

On the other hand, the present applicant has disclosed a method for producing the target compound of the present invention, an optically active 1-(2-trifluoromethylphenyl) ethanol, by optical resolution of a corresponding racemic phthalic half ester with an optically active 1-phenylethylamine (cf. Patent Document 2).

Patent Document 1: International Publication No. 2007/030359

Patent Document 2: Japanese Laid-Open Patent Publication No. 2007-106702

Non Patent Document 1: Tetrahedron: Asymmetry (U.K.), 2003, Vol. 14, P. 3581-3587

DISCLOSURE OF THE INVENTION

As described above, there has not been found any purification method for improving the optical purity of the optically active 1-(2-trifluoromethylphenyl)ethanol efficiently by simple operation. It is therefore an object of the present invention to provide an industrial purification method of an optically active 1-(2-trifluoromethylphenyl)ethanol.

As a result of extensive researches made in view of the above problems, the present inventors have found that the recrystallization of an optically active 1-(2-trifluoromethylphenyl)ethanol from an aliphatic hydrocarbon solvent allows the optically active 1-(2-trifluoromethylphenyl)ethanol to be preferentially deposited in optically pure crystal and thereby leads to a dramatic improvement in the optical purity of the optically active 1-(2-trifluoromethylphenyl)ethanol. The present inventors have also found that the deposited crystal can be obtained with very high chemical purity and high recovery.

As mentioned above, it is known that the optical purity of any of the various similar compounds cannot be improved efficiently only by recrystallization. The present inventors have however found, contrary to expectations, that it is possible to purify the optically active 1-(2-trifluoromethylphenyl)ethanol efficiently and advantageously on a large scale by recrystallization thereof from a specific solvent.

The present inventors have especially found that, among various kinds of aliphatic hydrocarbon solvents, the use of n-heptane leads to a significant improvement in the efficiency of recrystallization of the optically active 1-(2-trifluoromethylphenyl)ethanol. The present inventors have also found that the optically active 1-(2-trifluoromethylphenyl)ethanol can be purified on a large scale at a high recovery rate by using 2 mL to 10 mL of the aliphatic hydrocarbon solvent per 1 g of the optically active 1-(2-trifluoromethylphenyl)ethanol. The present inventors have further found that, although the optically active 1-(2-trifluoromethylphenyl)ethanol has a melting point close to room temperature (the melting point of the optically pure 1-(2-trifluoromethylphenyl)ethanol (of 100% ee (enantiomer excess)) is in the range of 30 to 40° C.), the recrystallization of the optically active 1-(2-trifluoromethylphenyl)ethanol can be performed sufficiently at an aging temperature of −20 to +10° C. so that the adoption of such temperature conditions enables a significant reduction of load on cooling equipment in industrial application.

In this way, the particularly useful industrial purification method of the optically active 1-(2-trifluoromethylphenyl) ethanol have been found by the present inventors. The present invention is based on the above findings.

According to the present invention, there is provided a method for purifying an optically active 1-(2-trifluoromethylphenyl)ethanol represented by the formula (1), comprising: recrystallizing the optically active 1-(2-trifluoromethylphenyl)ethanol from an aliphatic hydrocarbon solvent

[Chem. 1]

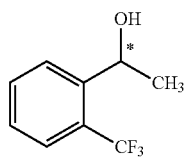

[1]

where * denotes an asymmetric carbon.

DETAILED DESCRIPTION

The advantages of the present invention over the earlier technologies will be described below.

The present invention is advantageous over Non-Patent Document 1 in that there is no need for any additive to form a complex and no need for any operation to recover the target compound from the complex after the recrystallization.

Further, the target optically active 1-(2-trifluoromethylphenyl)ethanol of the present invention can be specifically purified to much higher optical purity and chemical purity by recrystallization thereof from an aliphatic hydrocarbon solvent than similar compounds such as optically active 1-(3,5-bistrifluoromethylphenyl)ethanol, optically active 1-(3-trifluoromethylphenyl)ethanol and optically active 1-(4-trifluoromethylphenyl)ethanol. The recrystallization is easy in operation and is thus industrially easily realizable in combination with suitable purification conditions.

The present invention is also advantageous over Patent Document 2 in that there is no need to convert the target compound to a derivative thereof and to use an optical resolution agent.

The purification method of the optically active 1-(2-trifluoromethylphenyl)ethanol according to the present invention will be described below in detail.

The detailed procedure of the recrystallization purification is as follows.

A crude product (low optical purity product) of the optically active 1-(2-trifluoromethylphenyl)ethanol is added to a recrystallization solvent and dissolved by heating in the recrystallization solvent. The resulting solution is cooled to and aged at an aging temperature, thereby depositing a crystal of the optically active 1-(2-trifluoromethylphenyl)ethanol. The optically active 1-(2-trifluoromethylphenyl)ethanol is obtained as a purified product (very high optical purity product) by recovering the deposited crystal and removing the recrystallization solvent.

In the formula [1], * denotes an asymmetric carbon of the optically active 1-(2-trifluoromethylphenyl)ethanol. The absolute configuration of the asymmetric carbon can be either R-configuration or S-configuration.

There is no particular restriction on the optical purity of the optically active 1-(2-trifluoromethylphenyl)ethanol represented by the formula [1]. The optical purity of the optically active 1-(2-trifluoromethylphenyl)ethanol represented by the formula [1] is generally 50% ee or higher, preferably 70% ee or higher, more preferably 90% ee or higher.

In the present invention, the recrystallization of the optically active 1-(2-trifluoromethylphenyl)ethanol from an aliphatic hydrocarbon solvent is particularly effective when the optical purity of the optically active 1-(2-trifluoromethylphenyl)ethanol before the purification is in the range of 90 to 98% ee. It is an especially preferred embodiment of the present invention to recrystallize the optically active 1-(2-trifluoromethylphenyl)ethanol of such optical purity from the aliphatic hydrocarbon solvent so that the optical purity of the optically active 1-(2-trifluoromethylphenyl)ethanol can be improved significantly by simple operation and that the optically active 1-(2-trifluoromethylphenyl)ethanol can be obtained with high recovery after the purification. As a matter of course, the optically active 1-(2-trifluoromethylphenyl)ethanol of higher than 98% ee optical purity can be further purified. It is, however, not industrially easy to use the optical active 1-(2-trifluoromethylphenyl)ethanol having an optical purity of higher than 98% ee before the purification.

There is no particular restriction on the production process of the optically active 1-(2-trifluoromethylphenyl)ethanol represented by the formula [1]. One typical example of the production process of the optically active 1-(2-trifluoromethylphenyl)ethanol represented by the formula [1] is that shown in Scheme 1 (cf. Reference examples 1 and 2) and, more specifically, to form 2'-(trifluoromethyl)acetophenone by cross coupling reaction of industrially available 2-(trifluoromethyl)benzoylchloride and methyl magnesium chloride with the use of iron (III) acetylacetonate as a catalyst (cf. "Tetrahedron Letters (U.K.), 1987, Vol. 28, No. 18, P. 2053-2056"), and then, subject the acetophenone compound to asymmetric reduction in an alcohol solvent under a hydrogen gas atmosphere in the presence of a ruthenium complex having an optically active BINAP and an optically active diamine as asymmetric ligands and a base. The asymmetric reduction can be carried out by various techniques as disclosed in "Catalytic Asymmetric Synthesis, Second Edition, 2000, Wiley-VCH, Inc.".

Scheme 1

[Chem. 2]

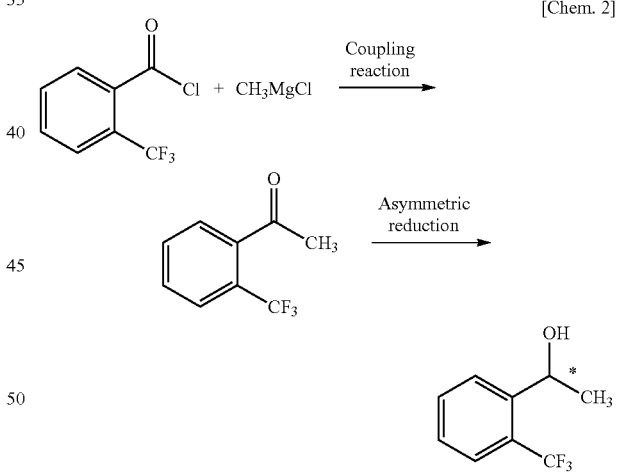

Examples of the recrystallization solvent are aliphatic hydrocarbon solvents such as n-pentane, n-hexane, c-hexane, n-heptane, n-octane, n-nonane, n-decane, n-undecane, n-dodecane and petroleum ether. Among others, n-hexane, n-heptane and n-octane are preferred. Particularly preferred is n-heptane. These recrystallization solvents can be used solely or in combination thereof. The target compound cannot be efficiently deposited in crystal form and recovered with very high optical purity and chemical purity and high efficiency with the use of any solvents other than the aliphatic hydrocarbon solvents, such as aromatic hydrocarbon solvents e.g. toluene, mixed xylene etc., methylene chloride, t-butyl methyl ether, acetone, ethyl acetate, acetonitrile, ethanol and water (cf. Comparative Examples). Among various kinds of aliphatic hydrocarbon solvents, the use of n-heptane leads to a significant improvement in recrystallization efficiency.

It suffice that the amount of the aliphatic hydrocarbon solvent used is 1 mL or more per 1 g of a crude product of the optically active 1-(2-trifluoromethylphenyl)ethanol represented by the formula [1]. The amount of the aliphatic hydrocarbon solvent used is preferably 2 to 20 mL, more preferably 2 to 12 mL, still more preferably 2 to 10 mL, per 1 g of the crude product of the optically active 1-(2-trifluoromethylphenyl)ethanol represented by the formula [1]. If no solvent is used or if the amount of the aliphatic hydrocarbon solvent is less than 1 mL, the deposited crystal is low in flowability so that it is difficult to recover the crystal by recovery operation such as filtration. Further, the crystal can be deposited from the solution without any problem by leaving the solution still but cannot always be deposited from the solution efficiently by stirring the solution if the amount of the aliphatic hydrocarbon solvent is less than 2 mL. If the amount of the aliphatic hydrocarbon solvent exceeds 20 mL, the recovery of the crystal becomes lowered. When the amount of the aliphatic hydrocarbon solvent is in the particularly preferable range of 2 to 10 mL, the crystal can be deposited from the solution by stirring the solution industrially advantageously and efficiently and can be recovered at a high recovery rate.

The heat dissolving temperature is not particularly restricted and is generally set to lower than or equal to a boiling point of the recrystallization solvent, preferably 20 to 50° C., more preferably 30 to 40° C.

The cooling speed is not also particularly restricted and is generally set to 200° C. or lower per hour, preferably 150° C. or lower per hour, more preferably 100° C. or lower per hour.

It suffices that the aging temperature is in the range of −60 to +15° C. The aging temperature is preferably −40 to +10° C., more preferably −20 to +10° C. If the aging temperature is lower than −60° C., there arises large load on cooling equipment in industrial application. If the aging temperature is higher than +15° C., the crystal does not get deposited favorably. Further, the optical purity of the crystal tends to be slightly lowered if the aging temperature is lower than −40° C. If the aging temperature is higher than +10° C., the recovery of the crystal becomes lowered. When the aging temperature is in the particularly preferable range of −20 to +10° C., the load on cooling equipment can be reduced significantly in industrial application.

The aging time is not particularly restricted and is generally set to 0.1 to 24 hours. The aging time varies depending on the purification conditions. It is preferable to monitor the remaining amount of the crystal dissolved in the solution during the aging by any analytical means such as gas chromatography, liquid chromatography or NMR and determine the end point of the aging when the crystal deposition amount gets almost stabilized.

In the recrystallization, the crystal can be deposited more efficiently with the addition of a seed crystal during the cooling or aging.

There is no particular restriction on the amount of the seed crystal added. The amount of the seed crystal added is generally 0.0001 g or more, preferably 0.0002 to 0.1 g, more preferably 0.0004 to 0.05 g, per 1 g of the optically active 1-(2-trifluoromethylphenyl)ethanol represented by the formula [1].

There is also no particular restriction on the recovery operation. In general, the optically active 1-(2-trifluoromethylphenyl)ethanol of the formula [1] can be recovered with very high optical purity and high yield by filtering the deposited crystal, washing the crystal with a poor solvent and drying out the remaining recrystallization solvent and washing solvent. (It is optionally conceivable to cool the filter or poor solvent in advance and to conduct the drying under reduced pressure.) The chemical purity of the recovered crystal is very high as the optically pure crystal gets deposited in the recrystallization purification of the present invention. The recovered crystal may be subjected to activated carbon treatment or distillation as needed. The optically and chemically pure product can be obtained by repeatedly performing the recrystallization purification. Further, the aliphatic hydrocarbon solvent used as the recrystallization solvent can be recovered with high yield by distillation of the filtrate/wash liquid. The same level of purification efficiency is secured even by the reuse of the recovered hydrocarbon solvent.

The present invention will be described in more detail below by way of the following examples. It should be noted that these examples are illustrative and are not intended to limit the present invention thereto.

REFERENCE EXAMPLE 1

Coupling Reaction (The material charge and reaction steps were conducted under a nitrogen atmosphere.)

To 500 mL of tetrahydrofuran, added was 417 g (2.00 mol, 1.00 eq) of 2-(trifluoromethyl)benzoyl chloride represented by the following formula and 21.2 g (0.06 mol, 0.03 eq) of iron (III) acetylacetonate.

[Chem. 3]

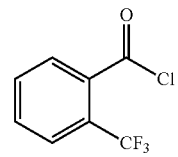

The resulting solution was admixed with 1.14 L (2.39 mol, 1.20 eq) of a 2.10 M solution of methyl magnesium chloride in tetrahydrofuran at a controlled temperature of 9° C. or lower under ice cooling and stirred for one night at room temperature. As a result of analysis of the post-reaction solution by gas chromatography, the conversion rate of the reaction was determined as 98%. After that, 670 mL (0.67 mol, 0.34 eq) of 1N hydrochloric acid was added to the post-reaction solution under ice cooling. The solution was stirred for 15 minutes at room temperature, left still, and then, separated into an organic phase and an aqueous phase. The aqueous phase was wasted. The organic phase was admixed with 250 mL (0.50 mol, 0.25 eq) of a 2N aqueous sodium hydroxide solution and stirred for 2 hours and 20 minutes at room temperature (so as to thereby cause hydrolysis of unreacted 2-(trifluoromethyl)benzoyl chloride). Further, the organic phase was admixed with 250 mL of a 10% aqueous sodium chloride solution. The resulting solution was left still and separated into an organic phase and an aqueous phase. The organic phase was recovered. The aqueous phase was extracted with 250 mL of toluene. The extract was left still and separated into an organic phase and an aqueous phase. The organic phase was recovered. (As the separability of the organic phase from the aqueous phase was slightly poor, the organic phase was subjected to cerite filtration; and the cerite residue was washed with 100 mL of toluene.) The recovered organic phases were combined together and quantified by $^{19}$F-NMR (internal standard method) as containing 299 g (1.59 mol, yield: 80%) of 2'-(trifluoromethyl)acetophenone represented by the following formula.

[Chem. 4]

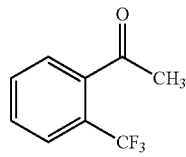

The combined organic phase was concentrated under reduced pressure and subjected to simple distillation (boiling point: 79 to 85° C., reduced pressure: 1.8 kPa), thereby yielding 279 g of a crude product. The yield of the crude product was 74%. The gas-chromatographic purity of the crude product was 99.2%. The whole of the crude product was subjected to fractional distillation (boiling point: 82 to 85° C., reduced pressure: 1.8 kPa), thereby recovering 251 g of a purified product. The recovery of the purified product was 90%. The gas-chromatographic purity of the purified product was 99.7%. The instrumental analytical data of the recovered purified product is indicated below.

$^1$H-NMR [reference material: $(CH_3)_4Si$, deutrated solvent: $CDCl_3$] δ ppm: 2.58 (s, 3H), 7.46 (Ar—H, 1H), 7.58 (Ar—H, 2H), 7.72 (Ar—H, 1H).

$^{19}$F-NMR [reference material: $C_6F_6$, deutrated solvent: $CDCl_3$] δ ppm: 103.56 (s, 3F).

REFERENCE EXAMPLE 2

Asymmetric Reduction (The material charge step was conducted under a nitrogen atmosphere. The operation of pressure decrease by degassing and pressure increase by nitrogen gas introduction was repeatedly conducted in the respective stages of the material charge step.)

To 100 mL of dehydrated i-propanol, added was 0.09 g (0.08 mmol, 0.00005 eq) of a ruthenium complex $RuCl_2[(S)$-binap][(S)-daipen] represented by the following formula and 0.50 g (4.46 mmol, 0.003 eq) of t-butoxy potassium.

[Chem. 5]

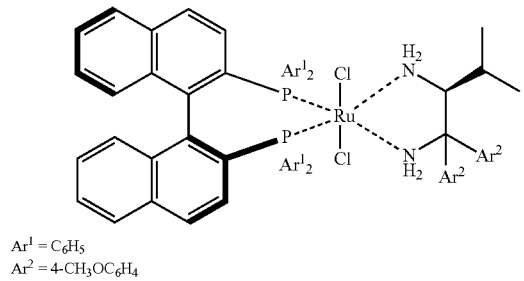

$Ar^1 = C_6H_5$
$Ar^2 = 4\text{-}CH_3OC_6H_4$

The resulting mixture was stirred for 1 hour at 50° C. (for preparation of an asymmetric catalyst solution).

A pressure-resistant reaction vessel of stainless steel (SUS) was charged with 4.00 g (35.6 mmol, 0.022 eq) of t-butoxy potassium, 300 g (1.59 mol, 1.00 eq) of 2'-(trifluoromethyl) acetophenone represented by the following formula and 1.50 L of dehydrated i-propanol, followed by adding thereto the whole of the above-prepared asymmetric catalyst solution.

[Chem. 6]

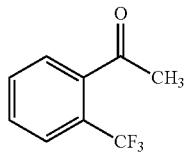

The resulting reactant solution was stirred for one night at 40° C. under a hydrogen gas atmosphere (1.8 MPa). As a result of analysis of the post-reaction solution by gas chromatography, the conversion rate of the reaction was determined as 100%. The post-reaction solution was then concentrated under reduced pressure. The thus-obtained residue was directly subjected to simple distillation (boiling point: 77° C., reduced pressure: 0.8 kPa), thereby yielding 273 g of a crude product of an optically active 1-(2-trifluoromethylphenyl)ethanol represented by the following formula.

[Chem. 7]

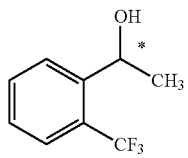

The yield of the crude product was 90%. The optical purity of the crude product was 97.4% ee (rich in R-configuration). The chemical purity of the crude product was 96.0% or higher.

$^1$H-NMR [reference material: $(CH_3)_4Si$, deutrated solvent: $CDCl_3$] δ ppm: 1.49 (d, 6.4 Hz, 3H), 1.99 (br, 1H), 5.33 (q, 6.4 Hz, 1H), 7.35-7.84 (Ar—H, 4H).

$^{19}$F-NMR [reference material: $C_6F_6$, deutrated solvent: $CDCl_3$] δ ppm: 103.43 (s, 3F).

The recrystallization purification operations of Examples 1 to 11, Comparative Examples 1 to 15 and Reference Examples 3 to 10 were carried out in the same manner. By way of example, the operation procedure of Example 5 is explained below. It is herein noted that: an optically active 1-(3-trifluoromethylphenyl)ethanol and an optically active 1-(4-trifluoromethylphenyl)ethanol could be produced in the same manner as the optically active 1-(2-trifluoromethylphenyl)ethanol; and the optical purity of each of the produced compounds could be adjusted by mixing the produced compound with an optically pure product or a racemic body thereof at an arbitrary ratio.

EXAMPLE 5

Recrystallization Purification

To 150 mL of n-heptane, added was 50 g of the optically active 1-(2-trifluoromethylphenyl)ethanol (optical purity: 95.9% ee (rich in R-configuration), chemical purity: 97.7%) represented by the following formula.

[Chem. 8]

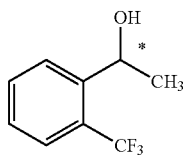

The optically active 1-(2-trifluoromethylphenyl)ethanol was dissolved in the n-heptane by heating at 40° C. The resulting solution was cooled, with stirring, to 2° C. over 30 minutes and subjected to aging at that temperature for 1 hour, thereby depositing a crystal. The deposited crystal was filtered through a pre-cooled filter, washed twice with 25 mL of cooled n-heptane, dried under reduced pressure. With this, 35.6 g of (R)-1-(2-trifluoromethylphenyl)ethanol represented by the following formula was obtained.

[Chem. 9]

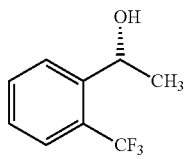

The recovery rate, optical purity and chemical purity of the (R)-1-(2-trifluoromethylphenyl)ethanol were 71%, 100% ee and 100%, respectively.

The results of Examples 1 to 11 and of Comparative Examples 1 to 15 regarding the purification of the optically active (R)-1-(2-trifluoromethylphenyl)ethanol are summarized in TABLE 1 and TABLE 2, respectively.

TABLE 1

Purification of optically active (R)-1-(2-trifluoromethylphenyl)ethanol (Examples)

| Example | Purification scale | Optical purity (chemical purity) before purification | Recrystallization solvent (mL/g) |
|---|---|---|---|
| 1 | 100 g | 90.8% ee (96.4%) | n-heptane (2 mL/g) |
| 2 | 50 g | 95.9% ee (97.7%) | n-heptane (2 mL/g) |
| 3 | 50 g | 95.9% ee (97.7%) | n-heptane (2 mL/g) |
| 4 | 400 g | 93.7% ee (97.8%) | n-heptane (3 mL/g) |
| 5 | 50 g | 95.9% ee (97.7%) | n-heptane (3 mL/g) |
| 6 | 50 g | 95.9% ee (97.7%) | n-heptane (5 mL/g) |
| 7 | 50 g | 95.9% ee (97.7%) | n-heptane (10 mL/g) |
| 8 | 50 g | 95.9% ee (97.7%) | n-heptane (30 mL/g) |
| 9 | 5 g | 95.9% ee (97.7%) | n-hexane (3 mL/g) |
| 10 | 5 g | 95.9% ee (97.7%) | c-hexane (3 mL/g) |
| 11 | 5 g | 95.9% ee (97.7%) | petroleum ether [a] (3 mL/g) |

TABLE 1-continued

Purification of optically active (R)-1-(2-trifluoromethylphenyl)ethanol (Examples)

| Example | Aging temperature (aging time) | Recovery rate | Optical purity (chemical purity) after purification |
|---|---|---|---|
| 1 | −16° C. (1 hr) | 79% | 99.7% ee (99.9%) |
| 2 | +2° C. (1.5 hr) | 78% | 99.8% ee (99.9%) |
| 3 | +10° C. (1.5 hr) | 66% | 100% ee (100%) |
| 4 | −37° C. (4 hr) | 90% | 99.3% ee (100%) |
| 5 | +2° C. (1 hr) | 71% | 100% ee (100%) |
| 6 | +2° C. (1.5 hr) | 65% | 100% ee (100%) |
| 7 | +2° C. (1.5 hr) | 57% | 100% ee (100%) |
| 8 | +2° C. (1.5 hr) | 9% | 100% ee (100%) |
| 9 | +2° C. (1.5 hr) | 62% | 99.4% ee (99.8%) |
| 10 | +10° C. (1.5 hr) | 29% | 100% ee (100%) |
| 11 | +2° C. (1.5 hr) | 43% | 100% ee (100%) |

[a] Boiling point: 30-60° C.

TABLE 2

Purification of optically active (R)-1-(2-trifluoromethylphenyl)ethanol (Comparative Examples)

| Comparative Example | Purification scale | Optical purity (chemical purity) before purification | Recrystallization solvent (mL/g) |
|---|---|---|---|
| 1 | 5 g | 95.9% ee (97.7%) | toluene (3 mL/g) |
| 2 | 5 g | 95.9% ee (97.7%) | toluene (1 mL/g) |
| 3 | 5 g | 95.9% ee (97.7%) | toluene (2 mL/g) |
| 4 | 5 g | 95.9% ee (97.7%) | toluene (0.5 mL/g) |
| 5 | 5 g | 95.9% ee (97.7%) | mixed xylene [a] (3 mL/g) |
| 6 | 5 g | 95.9% ee (97.7%) | mixed xylene [a] (1 mL/g) |
| 7 | 5 g | 95.9% ee (97.7%) | mixed xylene [a] (2 mL/g) |
| 8 | 5 g | 95.9% ee (97.7%) | mixed xylene [a] (0.5 mL/g) |
| 9 | 5 g | 95.9% ee (97.7%) | methylene chloride (2 mL/g) |
| 10 | 5 g | 95.9% ee (97.7%) | t-butyl methyl ether (2 mL/g) |
| 11 | 5 g | 95.9% ee (97.7%) | acetone (2 mL/g) |
| 12 | 5 g | 95.9% ee (97.7%) | ethyl acetate (2 mL/g) |
| 13 | 5 g | 95.9% ee (97.7%) | acetonitrile (2 mL/g) |
| 14 | 5 g | 95.9% ee (97.7%) | ethanol (2 mL/g) |
| 15 | 5 g | 95.9% ee (97.7%) | water (2 mL/g) |

| Comparative Example | Aging temperature (aging time) | Recovery rate | Optical purity (chemical purity) after purification |
|---|---|---|---|
| 1 | +2° C. (1.5 hr) | No deposition | — |

TABLE 2-continued

Purification of optically active (R)-1-(2-trifluoromethylphenyl)ethanol (Comparative Examples)

| | | | |
|---|---|---|---|
| 2 | +2° C. (1.5 hr) | Trace deposition | — |
| 3 | −37° C. (1.5 hr) | 45% | 100% ee (100%) |
| 4 | +2° C. (1.5 hr) | 44% | 100% ee (100%) |
| 5 | +2° C. (1.5 hr) | No deposition | — |
| 6 | +2° C. (1.5 hr) | Trace deposition | — |
| 7 | −37° C. (1.5 hr) | 40% | 100% ee (100%) |
| 8 | +2° C. (1.5 hr) | 48% | 100% ee (100%) |
| 9 | −16° C. (1.5 hr) | No deposition | — |
| 10 | −16° C. (1.5 hr) | No deposition | — |
| 11 | −16° C. (1.5 hr) | No deposition | — |
| 12 | −16° C. (1.5 hr) | No deposition | — |
| 13 | −16° C. (1.5 hr) | No deposition | — |
| 14 | −16° C. (1.5 hr) | No deposition | — |
| 15 | +2° C. (1.5 hr) | 93%[b] | 97.5% ee (99.0%) |

[a] o-xylene:m-xylene:p-xylene:ethylbenzene:other (styrene etc.) = 20:40:15:15:10
[b] The target compound was simply solidified without undergoing a uniformly dissolved state.

As is seen in TABLE 2 (Comparative Examples 1 to 15), it was difficult to recover the target compound in the case of using an aromatic hydrocarbon solvent or non-hydrocarbon organic solvent as the recrystallization solvent. The target compound was recovered from the solution, but at a low recovery rate, in the case of using a very small amount of the recrystallization solvent (the use of a large amount of the recrystallization solvent is accompanied by operation difficulties) and in the case of strongly cooling the solution. In the case of using water as the recrystallization solvent, the target compound was solidified without undergoing a uniformly dissolved state; and the optical purity of the target compound was not improved to a sufficient level.

By contrast, it has been shown in TABLE 1 (Examples 1 to 11) that it is possible to improve the optical purity and chemical purity of the target compound significantly and achieve the high recovery of the target compound by recrystallization purification of the target compound even under relatively moderate conditions.

Further, the results of Reference Examples 3 to 6 regarding the purification of the optically active (S)-1-(3-trifluoromethylphenyl)ethanol are summarized in TABLE 3.

TABLE 3

Purification of optically active (S)-1-(3-trifluoromethylphenyl)ethanol (Reference Examples)

| Reference Example | Purification scale | Optical purity (chemical purity) before purification | Recrystallization solvent (mL/g) |
|---|---|---|---|
| 3 | 5 g | 99.3% ee (100%) | n-heptane (3 mL/g) |
| 4 | 5 g | 99.3% ee (100%) | n-heptane (1 mL/g) |
| 5 | 5 g | 99.3% ee (100%) | n-heptane (1 mL/g) |

TABLE 3-continued

Purification of optically active (S)-1-(3-trifluoromethylphenyl)ethanol (Reference Examples)

| | | | |
|---|---|---|---|
| 6 | 5 g | 99.3% ee (100%) | No solvent |

| Reference Example | Aging temperature (aging time) | Recovery rate | Optical purity (chemical purity) after purification |
|---|---|---|---|
| 3 | +2° C. (1.5 hr) | No deposition | — |
| 4 | +2° C. (1.5 hr) | No deposition | — |
| 5 | −37° C. (1.5 hr) | Oil separation | — |
| 6 | −18° C. (12 hr) | No solidification | — |

The results of Reference Examples 7 to 10 regarding the purification of the optically active (R)-1-(4-trifluoromethylphenyl)ethanol are also summarized in TABLE 4.

TABLE 4

Purification of optically active (R)-1-(4-trifluoromethylphenyl)ethanol (Reference Examples)

| Reference Example | Purification scale | Optical purity (chemical purity) before purification | Recrystallization solvent (mL/g) |
|---|---|---|---|
| 7 | 5 g | 92.6% ee (99.8%) | n-heptane (2 mL/g) |
| 8 | 5 g | 92.6% ee (99.8%) | n-heptane (3 mL/g) |
| 9 | 5 g | 91.2% ee (99.7%) | n-heptane (2 mL/g) |
| 10 | 5 g | 91.6% ee (99.7%) | n-heptane (3 mL/g) |

| Reference Example | Aging temperature (aging time) | Recovery rate | Optical purity (chemical purity) after purification |
|---|---|---|---|
| 7 | −37° C. (1.5 hr) | —[a] | 93.4% ee (99.8%) |
| 8 | −37° C. (1.5 hr) | 82% | 94.9% ee (100%) |
| 9 | −16° C. (1.5 hr) | 85% | 94.8% ee (100%) |
| 10 | +2° C. (1.5 hr) | 59% | 97.5% ee (100%) |

[a] The recovery rate was not determined although the deposited crystal was recovered by filtration.

The invention claimed is:

1. A method for purifying an optically active 1-(2-trifluoromethylphenyl)ethanol represented by the formula [1], comprising: recrystallizing the optically active 1-(2-trifluoromethylphenyl)ethanol from an aliphatic hydrocarbon solvent

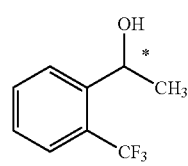

[1]

where * denotes an asymmetric carbon.

2. The method according to claim 1, wherein the aliphatic hydrocarbon solvent is at least one selected from the group consisting of n-pentane, n-hexane, c-hexane, n-heptane, n-octane, n-nonane, n-decane, n-undecane, n-dodecane and petroleum ether.

3. The method according to claim 1, wherein the aliphatic hydrocarbon solvent is at least one selected from the group consisting of n-hexane, n-heptane and n-octane.

4. The method according to claim 1, wherein the aliphatic hydrocarbon solvent is n-heptane.

5. The method according to claim 1, wherein the amount of the aliphatic hydrocarbon solvent used is in a range of 2 mL to 10 mL per 1 g of the optically active 1-(2-trifluoromethylphenyl)ethanol.

6. The method according to claim 1, wherein said recrystallizing is performed at an aging temperature of −20 to +10° C.

7. The method according to claim 1, wherein said recrystallizing is performed with the addition of a seed crystal.

* * * * *